(12) United States Patent
Kojima et al.

(10) Patent No.: US 9,277,934 B2
(45) Date of Patent: Mar. 8, 2016

(54) LIQUID INJECTION DEVICE AND SURGICAL INSTRUMENT INCLUDING LIQUID INJECTION DEVICE

(75) Inventors: Hideki Kojima, Matsumoto (JP); Hideyuki Takahashi, Omachi (JP)

(73) Assignee: Seiko Epson Corporation, Tokyo (JP)

( * ) Notice: Subject to any disclaimer, the term of this patent is extended or adjusted under 35 U.S.C. 154(b) by 618 days.

(21) Appl. No.: 13/212,138

(22) Filed: Aug. 17, 2011

(65) Prior Publication Data
US 2012/0046681 A1 Feb. 23, 2012

(30) Foreign Application Priority Data
Aug. 23, 2010 (JP) .................................. 2010-185851

(51) Int. Cl.
*A61B 17/3203* (2006.01)
*A61B 17/00* (2006.01)
*A61M 1/00* (2006.01)

(52) U.S. Cl.
CPC ... *A61B 17/3203* (2013.01); *A61B 2017/00402* (2013.01); *A61M 1/0066* (2013.01)

(58) Field of Classification Search
CPC .............. A61B 17/3203; A61B 2017/00154; A61B 2217/005; A61B 2217/007; A61B 2218/001; A61B 2218/007
USPC .................... 606/167; 604/48; 239/102.01
See application file for complete search history.

(56) References Cited

U.S. PATENT DOCUMENTS

| 3,526,219 | A * | 9/1970 | Balamuth | 600/565 |
|---|---|---|---|---|
| 5,197,485 | A * | 3/1993 | Grooters | 600/571 |
| 5,524,821 | A * | 6/1996 | Yie et al. | 239/10 |
| 6,030,399 | A * | 2/2000 | Ignotz et al. | 606/167 |
| 6,375,635 | B1 * | 4/2002 | Moutafis et al. | 604/43 |
| 7,901,374 | B2 * | 3/2011 | Seto et al. | 604/48 |
| 8,062,246 | B2 * | 11/2011 | Moutafis et al. | 604/43 |
| 2002/0177802 | A1* | 11/2002 | Moutafis et al. | 604/22 |
| 2004/0068291 | A1* | 4/2004 | Suzuki | 606/205 |
| 2008/0086077 | A1* | 4/2008 | Seto et al. | 604/48 |
| 2008/0114206 | A1* | 5/2008 | Edwards | 600/156 |
| 2011/0089256 | A1* | 4/2011 | Kojima et al. | 239/102.2 |

FOREIGN PATENT DOCUMENTS

| JP | 01-313047 | 12/1989 |
|---|---|---|
| JP | 2008-082202 | 4/2008 |
| JP | 2010-075589 | 4/2010 |
| JP | 2010-084564 | 4/2010 |

\* cited by examiner

*Primary Examiner* — Thomas McEvoy
*Assistant Examiner* — Julie A Szpira
(74) *Attorney, Agent, or Firm* — Workman Nydegger

(57) ABSTRACT

Liquid to be injected from an injection nozzle is supplied through a liquid supply channel toward the injection nozzle. Negative pressure for sucking the liquid injected from the injection nozzle through a suction port is produced by a suction unit and guided through a suction channel toward the suction port. A bypass channel which bypasses the liquid supply channel on the upstream side with respect to the injection nozzle and connects with the suction channel is provided. The bypass channel is opened and closed by an opening and closing unit. According to this structure, flow of unnecessary liquid from the injection nozzle can be reduced by opening the opening and closing unit while injection of liquid is stopping.

19 Claims, 6 Drawing Sheets

LIQUID INJECTION DEVICE AND SURGICAL INSTRUMENT INCLUDING LIQUID INJECTION DEVICE

This application claims the benefit of priority to Japanese Application No. 2010-185851 filed Aug. 23, 2010, which application is incorporated by reference in its entirety.

BACKGROUND

1. Technical Field

The present invention relates to a technology of injecting liquid from an injection nozzle.

2. Related Art

A liquid injection device developed in recent years injects pressurized liquid such as water and physiological salt water through an injection nozzle toward living tissue to incise or excise the living tissue. When used in surgery, this type of liquid injection device can selectively incise or excise only the target tissue such as internal organs without damaging vascular structures such as blood vessels, and thus can reduce injuries of the surrounding tissue. Accordingly, this device is expected to decrease the burden imposed on a patient receiving the surgery.

According to the liquid injection device having this structure, however, the visibility of the surgery target area deteriorates due to accumulation of liquid injected from the injection nozzle or blood flowing from the living tissue as liquids remaining on the surgery target area. For overcoming this problem, such a liquid injection device which has a suction port disposed in the vicinity of the injection nozzle and connected with a suction pump has been proposed (JP-A-1-313047). According to this device, the liquid or blood remaining on the surgery target area is sucked and discharged through the suction port brought near the surgery target area, so that sufficient visibility of the surgery target area can be secured.

In addition, such a liquid injection device which injects liquid from an injection nozzle not continuously but in pulses produced by periodically varying the flow of injection has been proposed (JP-A-2008-82202). This liquid injection device has a supply pump which pressurizes and supplies liquid toward a liquid chamber connected with the injection nozzle, and an actuator which varies the volume of the liquid chamber. The liquid injection device thus constructed pressurizes liquid within the liquid chamber and injects the liquid in pulses from the injection nozzle by rapidly decreasing the volume of the liquid chamber filled with liquid. According to the device which injects liquid in pulses, injection of only a small amount of liquid is required for incising or excising living tissue. Thus, reduction of the quantity of the liquid remaining on the surgery target area can be achieved.

According to this type of liquid injection device, however, liquid continuously flows from the injection nozzle and accumulates on the surgery target area even during suspension of incision or excision of living tissue. More specifically, in the case of the liquid injection device capable of injecting liquid in pulses, the supply pump keeps operating to maintain a sufficient pressure of liquid to be supplied to the liquid chamber even while the operation of the actuator is stopping (injection of pulsed liquid is stopping). In this case, liquid pressurized and supplied from the supply pump continuously flows from the injection nozzle. Even when the operation of the supply pump is stopped, the liquid keeps flowing from the injection nozzle until the time when the pressure of the liquid pressurized and supplied toward the liquid chamber sufficiently drops, which pressure drop cannot be produced immediately after the stop of the supply pump. Thus, the liquid remaining on the surgery target area as liquid not used for incision or excision of the living tissue (that is, unnecessary liquid) is required to be sucked and removed, which increases labor for the user.

SUMMARY

An advantage of some aspects of the invention is to provide a technology of a liquid injection device which injects liquid from an injection nozzle and is capable of reducing unnecessary flow of liquid from the injection nozzle for solving the aforementioned problems arising from the related arts.

A liquid injection device according to an aspect of the invention includes: an injection nozzle from which liquid is injected; a suction port through which the injected liquid is sucked; a liquid supply channel through which the liquid to be injected from the injection nozzle is supplied toward the injection nozzle; a suction unit which produces negative pressure for sucking the liquid through the suction port; a suction channel through which the negative pressure produced by the suction unit is guided toward the suction port; a bypass channel which bypasses the liquid supply channel on the upstream side with respect to the injection nozzle and connects with the suction channel; and an opening and closing unit which opens and closes the bypass channel.

According to the liquid injection device of this aspect of the invention, the liquid to be injected from the injection nozzle flows through the liquid supply channel to be supplied to the injection nozzle. The negative pressure developed by the suction unit for sucking the liquid injected from the injection nozzle through the suction port is guided through the suction channel toward the suction port. The liquid injection device of this aspect of the invention further includes the bypass channel which bypasses the liquid supply channel on the upstream side with respect to the injection nozzle and connects with the suction channel. The bypass channel is opened and closed by the opening and closing unit.

According to the liquid injection device having this structure in this aspect of the invention, the liquid within the liquid supply channel sucked by the suction unit flows through the bypass channel when the opening and closing unit is opened. In this condition, liquid supply to the injection nozzle can be stopped. Thus, flow of unnecessary liquid from the injection nozzle (liquid not injected toward the injection target) can be stopped by opening the opening and closing unit while injection of liquid is suspended, which eliminates the labor of sucking and discharging the unnecessary liquid performed by the operator.

Moreover, the liquid within the liquid supply channel can be discharged before reaching the injection nozzle by using the device structure (suction channel and suction unit) for sucking and discharging the liquid injected from the injection nozzle through the suction port. In this case, the unnecessary liquid flowing from the injection nozzle can be reduced without providing an additional discharging unit or the like for discharging the liquid within the liquid supply channel.

The liquid injection device of the above aspect may have the following structures. The liquid within the liquid supply channel is pressurized and supplied toward the injection nozzle by using a liquid pressurizing and supplying unit so that the liquid can flow from the injection nozzle. The pressure of the liquid flowing within the liquid supply channel is varied by the operation of a pressure varying unit on the downstream side with respect to the liquid pressurizing and supplying unit so that the liquid can be injected in pulses from the injection nozzle. The bypass channel is opened by the opening and closing unit when the pressure varying unit is not driven.

According to this structure, the pressure of the liquid pressurized and supplied by the liquid pressuring and supplying unit is also varied by the pressure varying unit, by which method the liquid can be injected in pulses from the injection nozzle. When injection of pulsed liquid is not required, the operation of the pressure varying unit is suspended. However, since the pressure of the liquid within the liquid supply channel is raised by the liquid pressurizing and supplying unit, the liquid still flows from the injection nozzle even after the stop of the pressure varying unit. According to this structure, flow of the liquid from the injection nozzle can be stopped by opening the opening and closing unit in accordance with the stop of the pressure varying unit.

Considering the necessity that injection of pulsed liquid from the injection nozzle with a desired force immediately after the start of the pressure varying unit (the necessity for rapid initiation of operation), it is preferable that the liquid pressurizing and supplying unit continuously pressurizes and supplies the liquid even while the pressure varying unit is not operating. According to this structure which opens the opening and closing unit in accordance with the stop of the pressure varying unit, flow of the liquid from the injection nozzle can be stopped even while the liquid pressurizing and supplying unit continues pressurization and supply of the liquid during non-operation of the pressure varying unit. Thus, rapid initiation of operation and reduction of unnecessary liquid from the injection nozzle can be both achieved.

According to the liquid injection device of the above aspect of the invention, the liquid pressurized and supplied by the liquid pressurizing and supplying unit may be stopped after or in synchronization with the time when the opening and closing unit opens the bypass channel.

The pressure of the liquid within the liquid supply channel is raised by the liquid pressurizing and supplying unit. In this case, flow of the liquid from the injection nozzle is not suspended immediately after the stop of the liquid pressurized and supplied by the liquid pressurizing and supplying unit. According to this structure, however, the pressure of the liquid within the liquid supply channel can be instantly lowered by opening the opening and closing unit before or in synchronization with the stop of the liquid pressurizing and supplying unit. Thus, flow of the unnecessary liquid from the injection nozzle after the stop of the liquid pressuring and supplying unit can be reduced.

When the period of the operation stop of the pressure varying unit is long, the liquid sucked by the suction unit without injection from the injection nozzle can be reduced for liquid saving during the stop of the liquid pressurized and supplied by the liquid pressurizing and supplying unit.

The liquid injection device of this aspect of the invention is applicable to a surgical instrument which incises or excises living tissue by using liquid injected from the liquid injection device toward the living tissue as a particularly preferable example. Therefore, another aspect of the invention is directed to a surgical instrument which injects liquid toward living tissue by using the liquid injection device of the above aspect of the invention.

According to the liquid injection device of this aspect of the invention, the liquid within the liquid supply channel sucked by the suction unit flows through the bypass channel when the opening and closing unit is opened. In this condition, supply of the liquid to the injection nozzle can be suspended. Thus, when incision or excision of living tissue is not performed, flow of unnecessary liquid (liquid not used for incision or excision of living tissue) from the injection nozzle can be stopped by opening the opening and closing unit. Accordingly, the liquid remaining on a surgery target area can be reduced, which eliminates the labor of sucking and discharging the liquid remaining on the surgery target area performed by the operator.

BRIEF DESCRIPTION OF THE DRAWINGS

The invention will be described with reference to the accompanying drawings, wherein like numbers reference like elements.

DESCRIPTION OF EXEMPLARY EMBODIMENT

Figure 1:
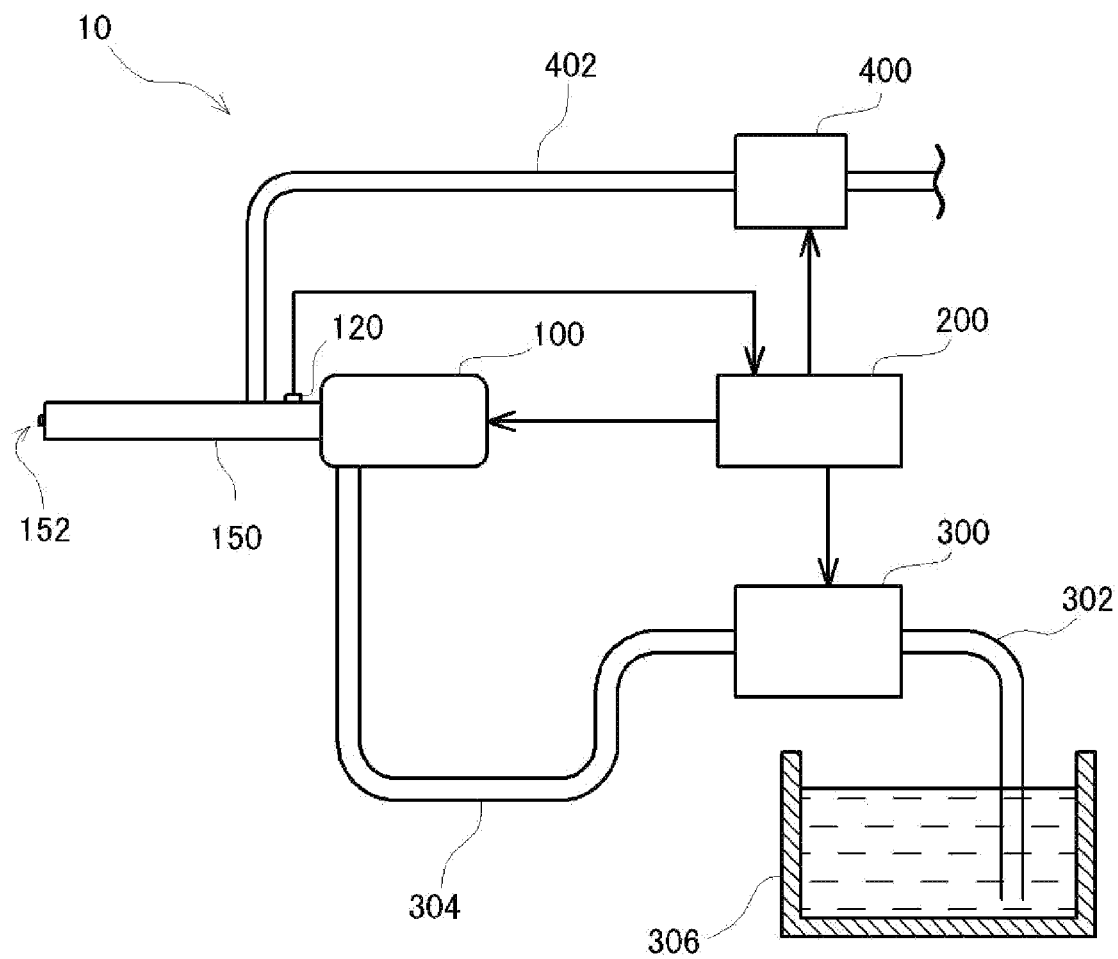
FIG. 1 illustrates the general structure of a liquid injection device according to an embodiment.

An embodiment according to the invention is hereinafter described in the following order for clarifying the details of the invention.
A. Device Structure
  A-1. Structure of Liquid Injection Device
  A-2. Structure of Injection Unit
  A-3. Structure of Channel Tube
B. Opening and Closing Operation of Opening and Closing Valve of Embodiment
C. Modified Example A. Device Structure A-1. Structure of Liquid Injection Device FIG. 1 illustrates the general structure of a liquid injection device 10 according to this embodiment. The liquid injection device 10 shown in the figure is an instrument used in a surgical method which incises or excises living tissue by injection of liquid such as water and physiological salt water toward the living tissue.

As illustrated in the figure, the liquid injection device 10 in this embodiment includes an injection unit 100 which injects liquid such as water and physiological salt water in pulses, a supply pump 300 which supplies liquid for injection to the injection unit 100, a liquid tank 306 which stores liquid for injection, a suction pump 400 which sucks liquid injected toward living tissue or other suction targets, a control unit 200 which controls the operations of the injection unit 100, the supply pump 300, and the suction pump 400, and other units. The suction pump 400 in this embodiment corresponds to a "suction unit" in the appended claims.

The supply pump 300 is connected with the liquid tank 306 via a liquid channel 302 to supply liquid sucked from the liquid tank 306 to the injection unit 100 through a supply tube 304. The supply pump 300 in this embodiment has two pistons sliding relative to each other within a cylinder. These two pistons slide in opposite phases in such a manner that one of the pistons advances during retreat of the other piston, thereby allowing liquid to be continuously pressurized and supplied to the injection unit 100 without break. The supply pump 300 for pressurizing and supplying liquid in this embodiment corresponds to a "liquid pressurizing and supplying unit" in the appended claims.

A cylindrical channel tube 150 is connected with the injection unit 100, and an injection nozzle 152 is provided at the tip of the channel tube 150. Liquid supplied from the supply pump 300 to the injection unit 100 is rapidly pressurized within the injection unit 100, and supplied through the channel tube 150 toward the injection nozzle 152 to be injected in pulses therefrom. The liquid injection device 10 in this embodiment has a pulse injection switch 120 on the outer surface of the channel tube 150 to start liquid injection when the operator turns on the pulse injection switch 120, and stop liquid injection when the operator turns off the pulse injection switch 120. The detailed structure of the injection unit 100 will be explained later.

The suction pump 400 is connected with a not-shown suction inlet provided in the vicinity of the injection nozzle 152 via a suction tube 402. When liquid injected from the injection nozzle 152 toward the living tissue, blood flowing from the living tissue or the like accumulates on a surgery target area (living tissue to be incised or excised and its surroundings), the visibility of the surgery target area deteriorates. According to this embodiment, however, the liquid or blood remaining on the surgery target area is sucked and discharged through the suction inlet by the operation of the suction pump 400. The detailed structure of the channel tube 150 provided with the suction inlet will be described later.

The control unit 200 controls the operations of the injection unit 100, the supply pump 300, and the suction pump 400. According to the liquid injection device 10 in this embodiment, the control unit 200 receives input of the state (ON or OFF) of the pulse injection switch 120 provided on the outer surface of the channel tube 150 as explained above, and controls the operation of the injection unit 100 in accordance with the state of the pulse injection switch 120.

A-2. Structure of Injection Unit

Figure 2A:
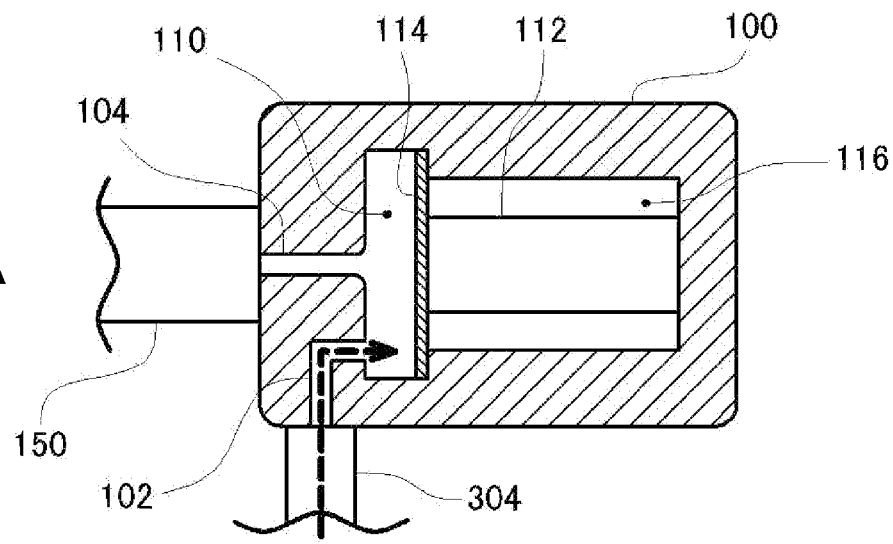
FIGS. 2A and 2B are cross-sectional views illustrating the detailed structure of an injection unit.
Figure 2B:
Figure 2B:
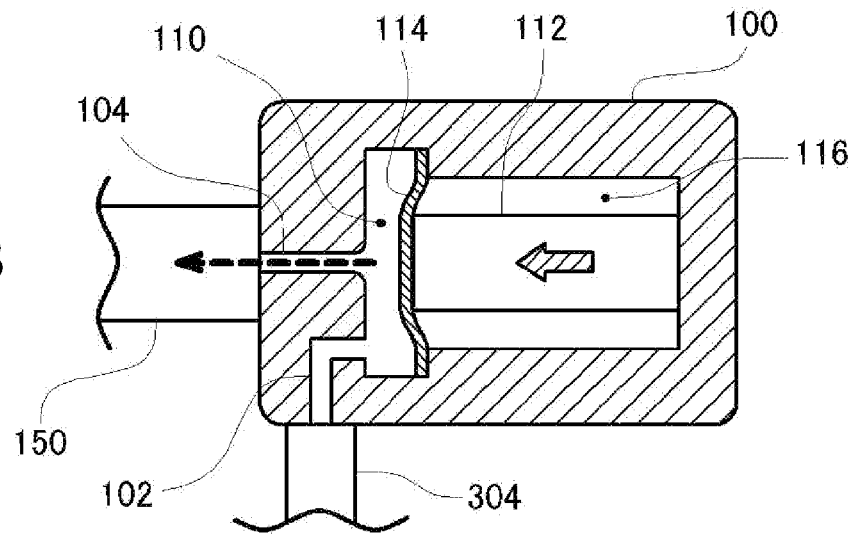

FIGS. 2A and 2B are cross-sectional views illustrating the detailed structure of the injection unit 100. As shown in FIG. 2A, the injection unit 100 contains a thin disk-shaped liquid chamber 110 filled with liquid for injection from the injection nozzle 152, an inlet channel 102 for guiding liquid supplied from the supply pump 300 toward the liquid chamber 110, an outlet channel 104 for guiding liquid within the liquid chamber 110 toward the channel tube 150, and others. One end of the liquid chamber 110 is defined by a diaphragm 114 formed by a thin metal plate or the like.

An actuator 112 constituted by a laminated piezoelectric device is accommodated in a cylindrical internal space 116 provided adjacent to the liquid chamber 110 with the diaphragm 114 interposed therebetween. One end of the actuator 112 is fixed to the bottom of the internal space 116 (surface opposed to diaphragm 114), and the other end of the actuator 112 contacts the diaphragm 114. The injection unit 100 having this structure injects liquid in accordance with the waveform of driving voltage applied to the actuator 112 by the following mechanism.

Before the driving voltage waveform is applied to the actuator 112 under the OFF condition of the pulse injection switch 120, the actuator 112 is not operating. In this condition, the liquid chamber 110 is filled with liquid supplied from the supply pump 300 as indicated by an arrow with a broken bold line in FIG. 2A. Since liquid is continuously supplied from the supply pump 300 without break as explained above, liquid within the liquid chamber 110 under the condition filled with liquid is pushed out toward the channel tube 150 even during operation stop of the actuator 112.

When the driving voltage waveform is applied to the actuator 112 in response to switching on of the pulse injection switch 120 under the condition of the liquid chamber 110 filled with liquid, the actuator 112 expands in accordance with increase in the driving voltage and presses (deforms) the diaphragm 114 toward the liquid chamber 110 as illustrated in FIG. 2B. By this deformation, the volume of the liquid chamber 110 decreases, which pressurizes the liquid within the liquid chamber 110. As a result, the liquid pressurized within the liquid chamber 110 flows through the outlet channel 104 and the channel tube 150 as indicated by an arrow with a bold broken line in FIG. 2B to be injected from the injection nozzle 152.

The liquid chamber 110 connects with the two paths of the inlet channel 102 and the outlet channel 104. In this case, the liquid pressurized within the liquid chamber 110 is expected to flow out not only through the outlet channel 104 but also through the inlet channel 102. However, based on the fact that the flow of liquid within a channel is chiefly determined by the length, the cross-sectional area of the channel or other conditions, liquid can be made to flow more easily from the outlet channel 104 than from the inlet channel 102 by appropriately determining the respective lengths and the cross-sectional areas of the inlet channel 102 and the outlet channel 104. The inlet channel 102 is a channel through which liquid pressurized and supplied from the supply pump 300 flows into the liquid chamber 110. Thus, this flow needs to be pushed back when the liquid within the liquid chamber 110 is made to flow therefrom through the inlet channel 102. However, such flow which prevents liquid from flowing out of the liquid chamber 110 through the outlet channel 104 does not exist in the outlet channel 104. Therefore, the liquid pressurized in the liquid chamber 110 flows exclusively from the outlet channel 104, and passes through the channel tube 150 to be injected at high speed from the injection nozzle 152 provided at the tip of the channel tube 150.

After injection of liquid in this manner, the actuator 112 contracts to its original length by a drop of the driving voltage, and restores the volume of the liquid chamber 110 to its original volume. As a result, liquid supplied from the supply pump 300 comes into the liquid chamber 110 to return to the condition shown in FIG. 2A. Then, the actuator 112 again expands in accordance with a rise of the driving voltage, and allows liquid pressurized in the liquid chamber 110 to be injected from the injection nozzle 152 as illustrated in FIG. 2B. By repeating these actions, the liquid injection device 10 in this embodiment injects liquid in pulses.

Injection of liquid in pulses refers to a condition of liquid injection with variable flow speed for the flow amount of liquid. The method for injection of liquid in pulses includes intermittent injection which repeats injection and stop of liquid. However, liquid injection may be performed by methods other than intermittent injection as long as they can vary the flow speed for the flow amount of liquid. The actuator 112 which varies the pressure of liquid in this embodiment corresponds to a "pressure varying unit" in the appended claims. In addition, the control unit 200 in this embodiment under which the action for injection of liquid in pulses by the operation of the actuator 112 is controlled corresponds to a "pulse generating unit" in the appended claims.

According to the liquid injection device 10 in this embodiment, the supply pump 300 keeps operating while the actuator 112 is stopping (injection of pulsed liquid from the injection nozzle 152 is stopping). In this case, the pressure of liquid supplied from the supply pump 300 to the injection unit 100 is maintained, and therefore liquid can be injected in pulses from the injection nozzle 152 with a desired force simultaneously with the start of the actuator 112 (turning on the pulse injection switch 120).

A-3. Structure of Channel Tube

Figure 3A:
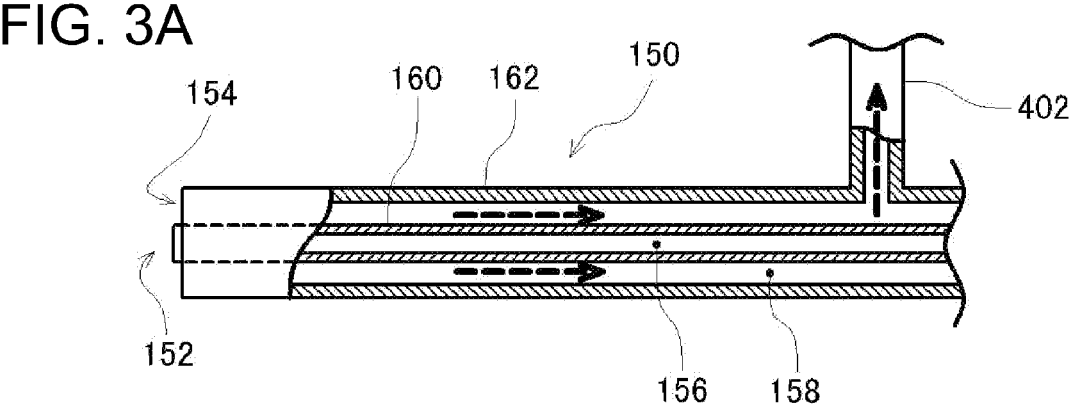
FIGS. 3A and 3B illustrate the detailed structure of a channel tube.
Figure 3B:
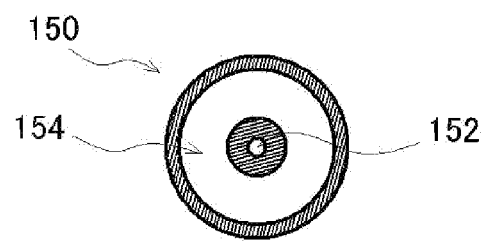

FIGS. 3A and 3B illustrate the detailed structure of the channel tube 150. As illustrated in FIG. 3A, the channel tube 150 has the injection nozzle 152 at the tip thereof as discussed above, and also a suction port 154 in the vicinity of the injection nozzle 152. According to this embodiment, the suction port 154 is provided in such a condition as to surround the injection nozzle 152 located at the center when the channel tube 150 is viewed from the injection nozzle 152 as illustrated in FIG. 3B.

As can be seen from FIG. 3A, the channel tube 150 has a dual-tube structure constituted by an internal tube 160 and an external tube 162. The inside of the internal tube 160 corresponds to an injection channel 156 connecting the outlet channel 104 of the injection unit 100 and the injection nozzle 152. The area disposed between the internal tube 160 and the external tube 162 corresponds to a suction channel 158 connecting the suction port 154 and the suction tube 402. As explained above, the liquid pressurized within the liquid chamber 110 of the injection unit 100 and flowing out of the outlet channel 104 passes through the injection channel 156 within the channel tube 150 and comes out of the injection nozzle 152 for injection. On the other hand, liquid or blood sucked through the suction port 154 by the operation of the suction pump 400 passes through the suction channel 158 and the suction tube 402 to be discharged therefrom. According to the liquid injection device 10 in this embodiment, the suction pump 400 operates in synchronization with the operation of the supply pump 300. The injection channel 156 and the supply tube 304 for guiding liquid toward the injection nozzle 152 in this embodiment correspond to a "liquid supply channel" in the appended claims. The suction channel 158 and the suction tube 402 for guiding a negative pressure developed by the suction pump 400 toward the suction port 154 in this embodiment correspond to a "suction channel" in the appended claims.

As explained above, according to the liquid injection device 10 in this embodiment, the supply pump 300 keeps operating while the operation of the actuator 112 is stopping. In this case, liquid is pushed out of the liquid chamber 110 and flows from the injection nozzle 152 by the amount corresponding to the supply from the supply pump 300 even when incision or excision of living tissue by injection of liquid from the injection nozzle 152 is not performed. Even when the supply pump 300 is suspended, flow of liquid from the injection nozzle 152 does not stop and accumulates on the surgery target area as unnecessary liquid until the time when the pressure of the liquid within the supply tube 304 sufficiently drops. According to the liquid injection device 10 in this embodiment, therefore, accumulation of unnecessary liquid flowing from the injection nozzle 152 on the surgery target area is avoided by the function of an opening and closing valve provided between the injection channel 156 and the suction channel 158 within the channel tube 150. This mechanism is now explained in detail.

B. Opening and Closing Operation of Opening and Closing Valve of Embodiment

Figure 4A:
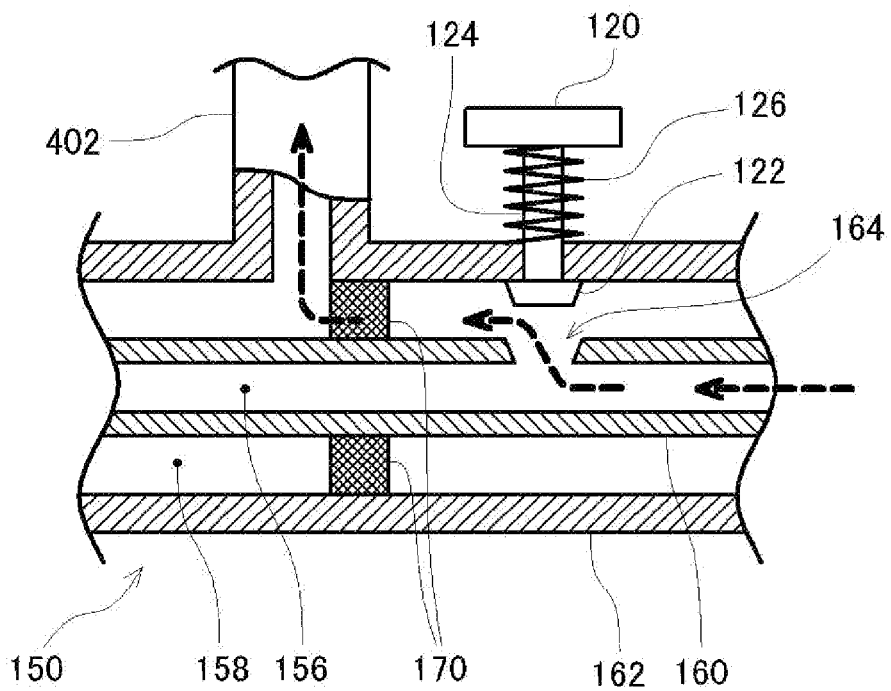
FIGS. 4A and 4B are cross-sectional views illustrating opened and closed conditions of an opening and closing valve in accordance with the condition of a pulse injection switch.
Figure 4B:
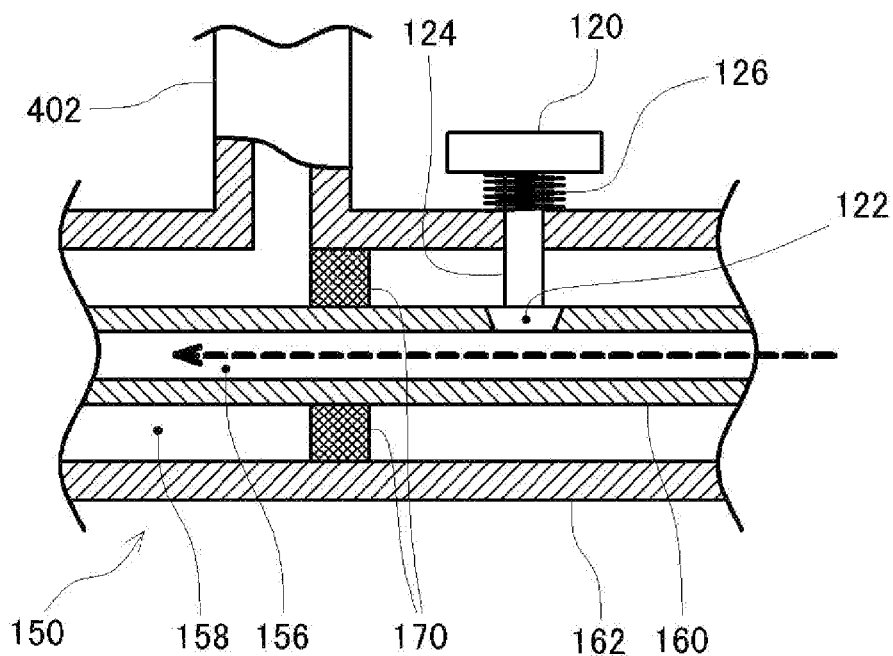

FIGS. 4A and 4B illustrate the opened and closed conditions of an opening and closing valve 122 provided within the channel tube 150 in the liquid injection device 10 in this embodiment. As illustrated in FIG. 4A, the internal tube 160 included in the channel tube 150 has a through hole 164 on the upstream side (injection unit 100 side) with respect to the suction tube 402 such that the inner injection channel 156 and the outer suction channel 158 can communicate with each other via the through hole 164. The pulse injection switch 120 is disposed on the outer surface of the external tube 162 at a position above the through hole 164. The pulse injection switch 120 is raised toward the outside (upper side) of the channel tube 150 by a spring 126, and joined with the opening and closing valve 122 for opening and closing the through hole 164 and with an interlocking pole 124. The through hole 164 which connects the injection channel 156 with the suction channel 158 to communicate with each other (bypass route) corresponds to a "bypass channel" in the appended claims.

When the pulse injection switch 120 is turned off and raised by the force of the spring 126 as illustrated in FIG. 4A, the opening and closing valve 122 is separated from the through hole 164 as the opened condition of the valve 122. In this condition, the liquid pushed from the liquid chamber 110 of the injection unit 100 toward the channel tube 150 and flowing through the injection channel 156 does not flow out of the injection nozzle 152 but flows through the through hole 164 into the suction channel 158 to which the negative pressure developed by the suction pump 400 is applied as indicated by an arrow with a bold broken line in the figure. Then, the liquid reaching the suction channel 158 flows through the suction tube 402 and the suction pump 400 to be discharged therefrom.

When the operator pushes the pulse injection switch 120 toward the inside of the channel tube 150 with resistance to the force of the spring 126 to turn on the pulse injection switch 120, the opening and closing valve 122 joined with the pulse injection switch 120 via the interlocking pole 124 lowers and closes the through hole 164 as the closed condition of the valve 122 as illustrated in FIG. 4B. In this condition, liquid pressurized within the liquid chamber 110 by the operation of the actuator 112 flows through the injection channel 156 to be injected from the injection nozzle 152 in pulses.

It is possible to dispose the through hole 164 and the opening and closing valve 122 on the downstream side with respect to the suction tube 402 (injection nozzle 152 side). According to the liquid injection device 10 in this embodiment, however, the through hole 164 and the opening and closing valve 122 are positioned on the upstream side with respect to the suction tube 402 for the following reasons. When tissue pieces are produced by incision or excision of living tissue, the tissue pieces sucked from the suction port 154 flow through the suction channel 158, wherefrom the tissue pieces are sucked and discharged by the suction tube 402 at a position before the through hole 164 and the opening and closing valve 122. In this case, deterioration of the suction capacity caused by clogging of the suction channel 158 with the tissue pieces or the like adhering to the opening and closing valve 122, or by decrease in the cross-sectional area of the suction channel 158 at the time of insertion of the interlocking pole 124 for closure of the opening and closing valve 122 can be avoided. Moreover, the area around the through hole 164 is not contaminated with disease-causing germs or the like contained in the liquid or tissue pieces sucked through the suction port 154 and adhering to the corresponding area. Thus, liquid injected from the injection nozzle 152 can be maintained in a clean condition.

As illustrated in FIGS. 4A and 4B, a filter 170 which transmits liquid in preference to solid may be provided between the suction tube 402 and the through hole 164. In this case, the tissue pieces sucked through the suction port 154 are blocked by the filter 170 and do not flow toward the through hole 164. Thus, adhesion of the tissue pieces or the like to the area around the through hole 164 can be further securely prevented. Even when the flow speed of the liquid passing through the through hole 164 and flowing toward the suction channel 158 is high, flow of the liquid from the suction port 154 in the reverse direction can be prevented by the filter 170 which reduces the flow speed of the liquid. In addition, a non-return valve may be provided in place of the filter 170. In this case, the material sucked through the suction port 154 does not pass through the through hole 164 toward the injection channel 156.

Accordingly, the liquid injection device 10 in this embodiment has the through hole 164 which connects the injection channel 156 for guiding the liquid for injection toward the injection nozzle 152 and the suction channel 158 for guiding the negative pressure produced by the suction pump 400 toward the suction port 154, and the opening and closing valve 122 which opens and closes the through hole 164. In this structure, when incision or excision of living tissue by using injected liquid from the injection nozzle 152 is not performed, liquid flowing within the injection channel 156 is made to flow toward the suction channel 158 by opening the opening and closing valve 122. In this condition, liquid does not flow from the injection nozzle 152, which reduces accumulation of liquid unnecessary for the surgery target area (liquid not used for incision or excision of living tissue). Therefore, the labor of sucking liquid remaining on the surgery target area performed by the operator can be eliminated.

As noted above, considering the necessity that injection of pulsed liquid from the injection nozzle 152 with a desired force immediately after the start of the actuator 112 (turning on the pulse injection switch 120), that is, the necessity for rapid initiation of operation, it is preferable that the supply pump 300 keeps operating even while the actuator 112 is not operating. According to the liquid injection device 10 in this embodiment, the pulse injection switch 120 and the opening and closing valve 122 are mechanically joined to each other. That is, when the pulse injection switch 120 is turned off, the opening and closing valve 122 is opened accordingly. Thus, even when the supply pump 300 is operating during non-operation of the actuator 112 (stop of incision or excision of living tissue), flow of liquid from the injection nozzle 152 can be stopped. Accordingly, accumulation of liquid unnecessary for the surgery target area can be prevented without delaying initiation of operation.

Moreover, liquid flowing within the injection channel 156 can be discharged on the upstream side with respect to the injection nozzle 152 by using the device structure (suction pump 400 and suction tube 402) for sucking and discharging the liquid and blood remaining on the surgery target area through the suction port 154. In this case, the necessity of providing an additional device structure (discharging pump and discharging tube) for discharging the liquid on the upstream side with respect to the injection nozzle 152 can be eliminated. Thus, reduction of unnecessary liquid remaining on the surgery target area can be easily achieved.

C. Modified Example

According to the embodiment described above, the opening and closing valve 122 is provided within the channel tube 150, and the pulse injection switch 120 disposed on the outer surface of the channel tube 150 is mechanically joined to the opening and closing valve 122. In this structure, the opening and closing valve 122 is opened or closed in accordance with the condition of the pulse injection switch 120 (OFF or ON). However, the opening and closing valve is not required to be positioned within the channel tube 150 but may be located on the upstream side with respect to the injection unit 100 as long as liquid supplied toward the injection nozzle 152 can be discharged on the upstream side with respect to the injection nozzle 152. The opening and closing operation of the opening and closing valve 122 may be interlocked with the condition of the pulse injection switch 120 under the control of the control unit 200. A modified example incorporating this structure is hereinafter described. In the description of the modified example, the parts which correspond to the same parts described in the embodiment have been given the same reference numbers, and the detailed explanation of those is not repeated.

Figure 5:
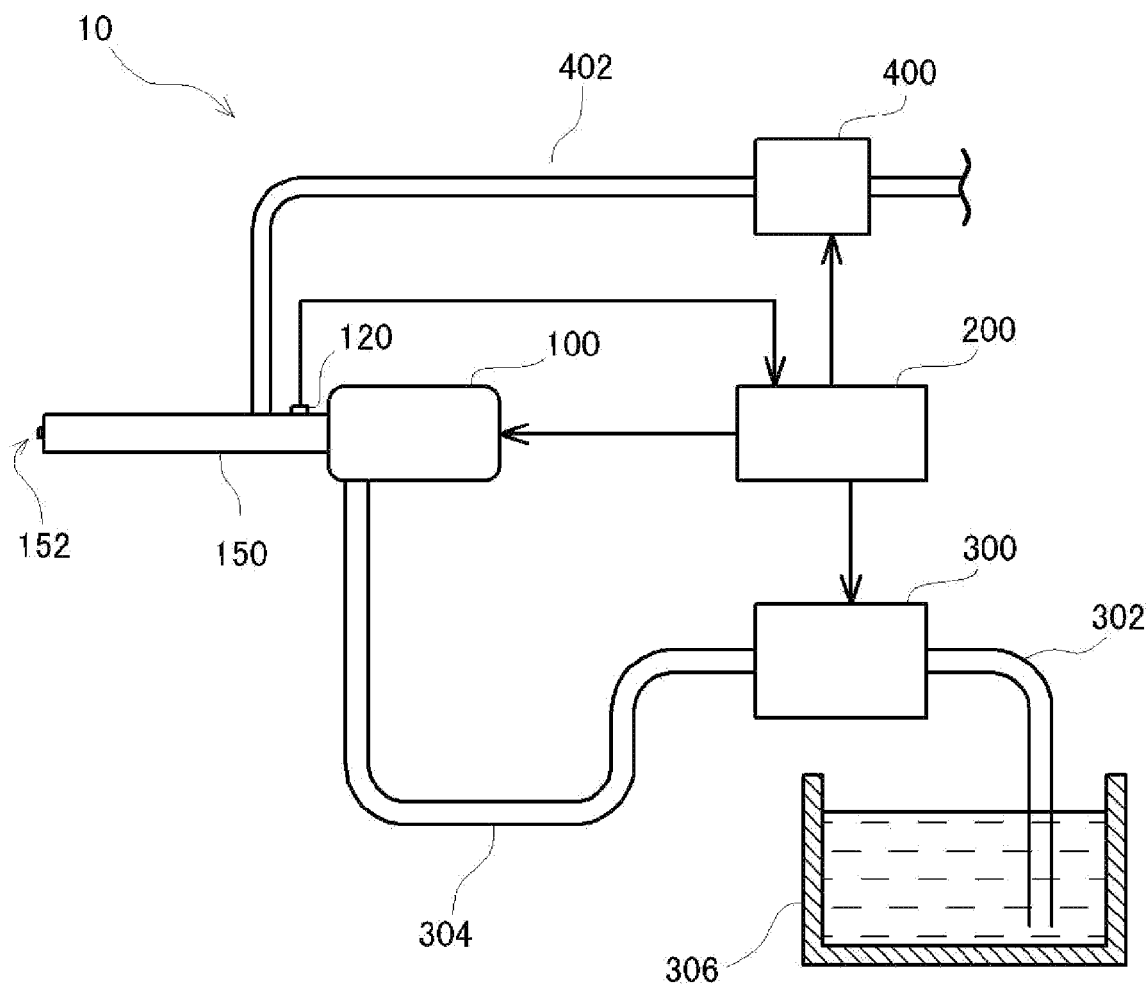
FIG. 5 illustrates the general structure of a liquid injection device according to a modified example.

FIG. 5 illustrates the general structure of the liquid injection device 10 according to the modified example. The liquid injection device 10 in this example does not have the parts such as the through hole 164 and the opening and closing valve 122 within the channel tube 150 included in the embodiment described above. Instead, the supply tube 304 for guiding liquid pressurized and supplied from the supply pump 300 toward the injection unit 100 is connected with the suction tube 402 for guiding the negative pressure developed by the suction pump 400 toward the suction channel 158 of the channel tube 150 via a connection tube 406. An opening and closing valve 404 is provided on the connection tube 406 to open and close the connection tube 406. The opening and closing operation of the opening and closing valve 404 is controlled by the control unit 200. The connection tube 406 for connecting the supply tube 304 and the suction tube 402 in the modified example corresponds to the "bypass channel" in the appended claims. The opening and closing valve 404 in the modified example corresponds to an "opening and closing unit" in the appended claims.

FIG. 5 does not show the pulse injection switch. According to the liquid injection device 10 in the modified example, the position of the pulse injection switch is not particularly limited as long as the condition of the pulse injection switch (ON or OFF) can be inputted to the control unit 200. For example, the pulse injection switch may be included in the control unit 200, or may be disposed in the vicinity of the foot of the operator so that the operator can operate the switch with foot.

Figure 6:
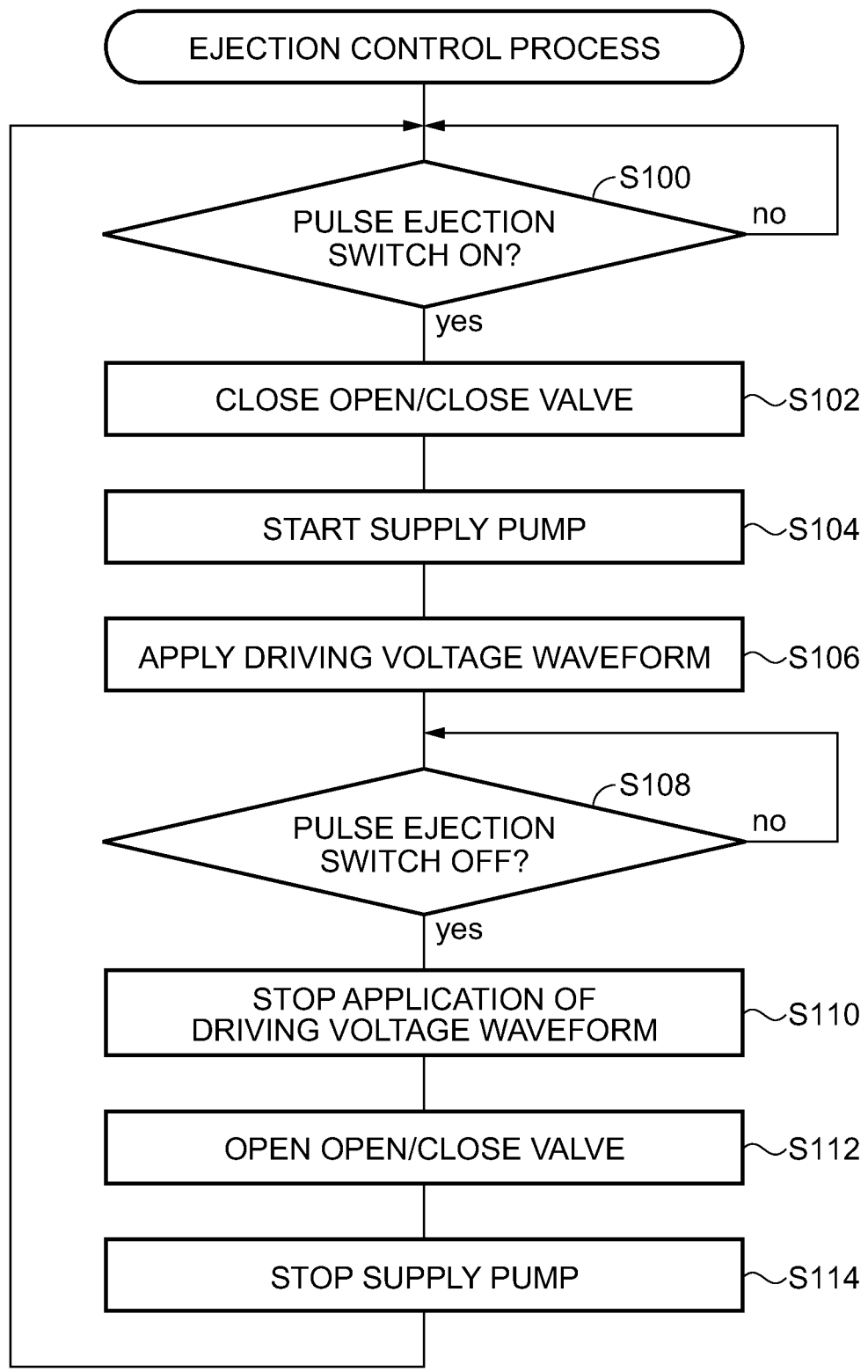
FIG. 6 is a flowchart showing the flow of an injection control process performed by the liquid injection device according to the modified example.

FIG. 6 is a flowchart showing the flow of an injection control process performed by the liquid injection device 10 in the modified example for injecting liquid from the injection nozzle 152. This process is executed under the control unit 200 which controls the operation of the liquid injection device 10.

As can be seen from the figure, the first step of the injection control process determines whether the pulse injection switch is turned on (step S100). As explained above, the condition of the pulse injection switch (ON or OFF) is inputted to the control unit 200 to determine whether the pulse injection switch is turned on or not based on the input. When it is determined that the pulse injection switch is turned off (step S100: NO), the determination in step S100 is repeated to keep monitoring whether the pulse injection switch is turned on.

When it is determined that the pulse injection switch is turned on (step S100: YES), the opening and closing valve 404 provided on the connection tube 406 is switched from the opened condition to the closed condition (step S102). After the closure of the opening and closing valve 404, the operation of the supply pump 300 is initiated (step S104). By the start of the supply pump 300, liquid sucked from the liquid tank 306 is pressurized and supplied toward the injection unit 100 as explained above, whereby the liquid chamber 110 in the injection unit 100 can be brought into the condition filled with liquid.

After the process of filling the liquid chamber 110 with liquid is completed, the driving voltage waveform is applied to the actuator 112 included in the injection unit 100 (step S106). As explained above, the actuator 112 expands in response to the rise of the driving voltage produced when the driving voltage waveform is applied to the actuator 112, in which condition the liquid is pressurized within the liquid chamber 110 and comes out from the injection nozzle 152 for injection. Then, the actuator 112 contracts in response to the reduction of the driving voltage, whereby the liquid chamber 110 is again brought into the condition filled with liquid supplied from the supply pump 300. These actions are repeated to perform injection of pulsed liquid from the injection nozzle 152.

After the start of liquid injection in this manner, it is now determined whether the pulse injection switch is turned off or not (step S108). When the pulse injection switch is still turned on (step S108: NO), the determination in step S108 is repeated to monitor whether the pulse injection switch is turned off.

When it is determined that the pulse injection switch is turned off (step S108: YES), the driving voltage waveform applied to the actuator 112 is suspended (S110). As a result, the operation of the actuator 112 (expansion) stops, whereby the injection of the pulsed liquid stops accordingly.

Then, the opening and closing valve 404 is switched from the closed condition to the opened condition (S112). When the opening and closing valve 404 is opened, the liquid within the supply tube 304 flows through the connection tube 406 toward the suction tube 402. Thus, the pressure of the liquid within the supply tube 304 can be immediately released.

After release of the pressure of the liquid within the supply tube 304 and suspension of the supply pump 300 (step S104), the process returns to the start of the injection control process to again determine whether the pulse injection switch 120 is turned on or not (step S100). When it is determined that the pulse injection switch 120 is turned on (step S100: YES), the opening and closing valve 404 is closed (step S102). Then, the operation of the supply pump 300 is initiated (step S104) for re-start of pressurization and supply of liquid toward the injection unit 100.

According to this modified example, the opening and closing valve 404 is opened after the stop of the actuator 112. However, the stop of the actuator 112 and the opening of the opening and closing valve 404 may be executed substantially at the same time. In addition, the supply pump 300 may be stopped not after the opening of the opening and closing valve 404 but simultaneously with the opening of the opening and closing valve 404.

Accordingly, in the case of the liquid injection device 10 in the modified example, the supply tube 304 for guiding liquid pressurized and supplied by the supply pump 300 toward the injection unit 100 is connected with the suction tube 402 for guiding the negative pressure produced by the suction pump 400 toward the suction channel 158 of the channel tube 150 via the connection tube 406 which can be opened and closed by the opening and closing valve 404. In this structure, when incision or excision of living tissue is not performed (pulsed liquid is not injected from the injection nozzle 152), the liquid within the supply tube 304 is made to flow toward the suction tube 402 by opening the opening and closing valve 404. In this condition, supply of liquid toward the injection nozzle 152 stops, wherefore unnecessary liquid flowing from the injection nozzle 152 onto the surgery target area does not accumulate thereon.

When the supply pump 300 is only stopped at the time of suspension of the operation of the actuator 112, high pressure is kept applying to the liquid within the supply tube 304. In this modified example, however, the pressure of the liquid within the supply tube 304 can be immediately released by opening the opening and closing valve 404. Thus, continuous flow of liquid from the injection nozzle 152 caused by the pressure remaining within the supply tube 304 after the suspension of the supply pump 300 stops, thereby reducing unnecessary liquid staying on the surgery target area.

Moreover, according to the liquid injection device 10 in the modified example, the supply pump 300 can be stopped during non-operation of the actuator 112. In this case, liquid discharged as unnecessary liquid not used for incision or excision of living tissue can be reduced and saved.

The invention is not limited to the embodiment and the modified example including all structures and parts described herein but may be practiced otherwise without departing from the scope of the invention.

For example, the following changes may be made. According to the modified example, flow of liquid from the injection nozzle 152 is suspended by stopping the supply pump 300 and opening the opening and closing valve 404 at the time of operation stop of the actuator 112. However, liquid may be made to flow from the injection nozzle 152 for cleaning the surgery target area even while the actuator 112 is not operating. For example, in such a structure which operates the supply pump 300 and closes the opening and closing valve 404 without driving the actuator 112 when the operator turns on a not-shown cleaning switch, liquid pressurized and supplied by the supply pump 300 can continuously flow from the injection nozzle 152 for cleaning the target surgery area.

In this case, liquid from the injection nozzle 152 can be immediately suspended by stopping the supply pump 300 and opening the opening and closing valve 404 similarly to the embodiment and the modified example when the cleaning switch is turned off by the operator.

What is claimed is:
1. A liquid injection device comprising:
a liquid supply channel that supplies a liquid towards an injection nozzle;
a liquid pressurizing and supplying unit which supplies pressurized liquid to the liquid supply channel;
a suction channel;
a bypass channel that is configured to connect the liquid supply channel and the suction channel; and
an opening and closing valve that is configured to open and close the bypass channel,
wherein the bypass channel is configured to guide the liquid in the liquid supply channel to the suction channel when the bypass channel is open, and
wherein, in operation, the liquid pressurizing and supplying unit continues to supply pressurized liquid regardless of whether the bypass channel is open or closed.
2. The liquid injection device according to claim 1, further comprising:
an injection pipe that includes the liquid supply channel and the injection nozzle,
wherein the bypass channel is connected to a portion of the injection pipe that is located upstream from the injection nozzle.

3. The liquid injection device according to claim 2, further comprising:
a suction pipe that includes the suction channel and a suction port that sucks the liquid,
wherein the injection pipe is located in the suction pipe.

4. The liquid injection device according to claim 1, further comprising:
a pulse generating unit which allows the liquid to be injected in pulses from the injection nozzle by varying a pressure of the liquid flowing within the liquid supply channel,
wherein the bypass channel is opened when the pulse generating unit is not driven.

5. The liquid injection device according to claim 1, further comprising:
a liquid supply control unit which is operable to stop the liquid pressurized and supplied by the liquid pressurizing and supplying unit after the opening and closing valve opens the bypass channel or in synchronization with a time when the opening and closing valve opens the bypass channel.

6. The liquid injection device according to claim 1, further comprising:
a filter that is located in the suction channel.

7. The liquid injection device according to claim 1,
wherein the liquid supply channel includes a liquid chamber which is able to fill the liquid,
and further comprising:
a pulse generating unit that allows the liquid to be injected in pulses from the injection nozzle by varying the pressure of the liquid in the liquid chamber.

8. The liquid injection device according to claim 7,
wherein the bypass channel is connected to a portion of the liquid supply channel located upstream from the liquid chamber.

9. The liquid injection device according to claim 7,
wherein the bypass channel is connected to a portion of the liquid supply channel located between the liquid chamber and the injection nozzle.

10. A surgical instrument comprising a liquid injection device according to claim 1.

11. A surgical instrument comprising a liquid injection device according to claim 2.

12. A surgical instrument comprising a liquid injection device according to claim 3.

13. A surgical instrument comprising a liquid injection device according to claim 4.

14. A surgical instrument comprising a liquid injection device according to claim 5.

15. A surgical instrument comprising a liquid injection device according to claim 6.

16. A surgical instrument comprising a liquid injection device according to claim 7.

17. A surgical instrument comprising a liquid injection device according to claim 8.

18. A surgical instrument comprising a liquid injection device according to claim 9.

19. The liquid injection device according to claim 1, wherein the bypass channel is in a closed state during a cutting operation involving the liquid injection device.

* * * * *